(12) United States Patent
Granados

(10) Patent No.: US 9,701,999 B2
(45) Date of Patent: Jul. 11, 2017

(54) MULTIPLEX METHYLATION-SPECIFIC AMPLIFICATION SYSTEMS AND METHODS

(71) Applicant: Abbott Molecular Inc., Des Plaines, IL (US)

(72) Inventor: Edward Granados, Vernon Hills, IL (US)

(73) Assignee: Abbott Molecular, Inc., Des Plaines, IL (US)

( * ) Notice: Subject to any disclaimer, the term of this patent is extended or adjusted under 35 U.S.C. 154(b) by 43 days.

(21) Appl. No.: 14/208,862

(22) Filed: Mar. 13, 2014

(65) Prior Publication Data

US 2014/0274735 A1    Sep. 18, 2014

Related U.S. Application Data

(60) Provisional application No. 61/782,370, filed on Mar. 14, 2013.

(51) Int. Cl.
*C12Q 1/68* (2006.01)
*C12P 19/34* (2006.01)

(52) U.S. Cl.
CPC ......... *C12Q 1/6858* (2013.01); *C12Q 1/6886* (2013.01); *C12Q 2600/154* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,130,238 A | 7/1992 | Malek et al. |
| 5,270,184 A | 12/1993 | Walker et al. |
| 5,283,174 A | 2/1994 | Arnold, Jr. et al. |
| 5,399,491 A | 3/1995 | Kacian et al. |
| 5,455,166 A | 10/1995 | Walker |
| 5,480,784 A | 1/1996 | Kacian et al. |
| 5,641,658 A | 6/1997 | Adams et al. |
| 5,695,934 A | 12/1997 | Brenner |
| 5,710,029 A | 1/1998 | Ryder et al. |
| 5,714,330 A | 2/1998 | Brenner et al. |
| 5,750,341 A | 5/1998 | Macevicz |
| 5,786,146 A | 7/1998 | Herman et al. |
| 5,814,447 A | 9/1998 | Ishiguro et al. |
| 5,824,518 A | 10/1998 | Kacian et al. |
| 5,912,148 A | 6/1999 | Eggerding |
| 5,925,517 A | 7/1999 | Tyagi et al. |
| 5,928,862 A | 7/1999 | Morrison |
| 6,130,073 A | 10/2000 | Eggerding |
| 6,150,097 A | 11/2000 | Tyagi et al. |
| 6,210,891 B1 | 4/2001 | Nyren et al. |
| 6,258,568 B1 | 7/2001 | Nyren |
| 6,303,305 B1 | 10/2001 | Wittwer et al. |
| 6,306,597 B1 | 10/2001 | Macevicz |
| 6,432,360 B1 | 8/2002 | Church |
| 6,485,944 B1 | 11/2002 | Church et al. |
| 6,511,803 B1 | 1/2003 | Church et al. |
| 6,534,274 B2 | 3/2003 | Becker et al. |
| 6,541,205 B1 | 4/2003 | Yokoyama et al. |
| 6,706,162 B1 | 3/2004 | Voss et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,108,974 B2 | 9/2006 | Ecker et al. |
| 7,115,400 B1 | 10/2006 | Adessi et al. |
| 7,169,560 B2 | 1/2007 | Lapidus et al. |
| 7,282,337 B1 | 10/2007 | Harris |
| 7,329,492 B2 | 2/2008 | Hardin et al. |
| 7,482,120 B2 | 1/2009 | Buzby et al. |
| 7,501,245 B2 | 3/2009 | Quake et al. |
| 7,524,629 B2 | 4/2009 | Olek et al. |
| 7,668,697 B2 | 2/2010 | Volkov et al. |
| 7,790,418 B2 | 9/2010 | Mayer |
| 7,972,820 B2 | 7/2011 | Mayer |
| 8,017,322 B2 | 9/2011 | Ecker et al. |
| 8,017,743 B2 | 9/2011 | Ecker et al. |
| 8,043,493 B2 | 10/2011 | Inaba et al. |
| 2004/0248090 A1* | 12/2004 | Olek .............. C12Q 1/6858 435/6.11 |
| 2005/0042638 A1 | 2/2005 | Arnold et al. |
| 2005/0130173 A1 | 6/2005 | Leamon et al. |
| 2005/0239101 A1 | 10/2005 | Sukumar et al. |
| 2006/0046265 A1 | 3/2006 | Becker et al. |
| 2006/0110741 A1 | 5/2006 | Asai et al. |
| 2008/0241951 A1 | 10/2008 | Battulga et al. |

(Continued)

FOREIGN PATENT DOCUMENTS

| | | |
|---|---|---|
| CN | 102424857 A | 4/2012 |
| DE | 10215770 A1 | 10/2003 |
| EP | 0684315 A1 | 11/1995 |
| WO | WO-9500669 A1 | 1/1995 |
| WO | WO-9515373 A2 | 6/1995 |
| WO | WO-9745560 A1 | 12/1997 |
| WO | WO-9746705 A1 | 12/1997 |
| WO | WO-9928498 A2 | 6/1999 |
| WO | WO-0018957 A1 | 4/2000 |
| WO | 0142493 A2 | 6/2001 |
| WO | WO-2006084132 A2 | 8/2006 |
| WO | 2007032748 A1 | 3/2007 |

OTHER PUBLICATIONS

Gonzalgo et al., "Rapid quantitation of methylation differences at specific sites using methylation-sensitive single nucleotide primer extension (Ms-SNuPE)," Nucleic Acids Research, 1997, vol. 25, No. 12, pp. 2529-2531.*

(Continued)

*Primary Examiner* — Young J Kim
(74) *Attorney, Agent, or Firm* — David A. Casimir; Casimir Jones S.C.

(57) ABSTRACT

The present invention relates to systems and methods for performing multiplex amplification reactions. In particular, the present invention relates to multiplex methylation-specific amplification systems and methods.

11 Claims, 1 Drawing Sheet

(56) References Cited

U.S. PATENT DOCUMENTS

| | | |
|---|---|---|
| 2008/0254474 A1 | 10/2008 | Laird et al. |
| 2009/0026082 A1 | 1/2009 | Rothberg et al. |
| 2009/0035777 A1 | 2/2009 | Kokoris et al. |
| 2009/0127589 A1 | 5/2009 | Rothberg et al. |
| 2010/0009365 A1 | 1/2010 | Laird et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0301398 A1 | 12/2010 | Rothberg et al. |
| 2011/0091882 A1 | 4/2011 | Granados et al. |

OTHER PUBLICATIONS

Adessi C., et al., "Solid Phase DNA Amplification: Characterisation of Primer Attachment and Amplification Mechanisms," Nucleic Acids Research, 2000, vol. 28 (20), pp. E87.

Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.

Bennett S.T., et al., "Toward the 1,000 Dollars Human Genome," Pharmacogenomics, 2005, vol. 6 (4), pp. 373-382.

Birren B., et al., eds., Genome Analysis—A Laboratory Manual, vol. 1, Cold Spring Harbor Laboratory Press, 1997, Table of Contents.

Brenner S., et al., "Gene Expression Analysis by Massively Parallel Signature Sequencing (MPSS) on Microbead Arrays," Nature Biotechnology, 2000, vol. 18 (6), pp. 630-634.

Dahl C., et al., "A Ligation Assay for Multiplex Analysis of CpG Methylation Using Bisulfite-Treated DNA," Nucleic Acids Research, 2007, vol. 35 (21), pp. e144 (8 pages).

Dodge J.E., et al., "De Novo Methylation of MMLV Provirus in Embryonic Stem Cells: Cpg versus Non-Cpg Methylation," Gene, 2002, vol. 289 (1-2), pp. 41-48.

Dressman D., et al., "Transforming Single Dna Molecules into Fluorescent Magnetic Particles for Detection and Enumeration of Genetic Variations," Proceedings of the National Academy of Sciences of the United States of America, 2003, vol. 100 (15), pp. 8817-8822.

Eads C.A., et al., "CpG Island Hypermethylation in Human Colorectal Tumors Is Not Associated with DNA Methyltransferase Overexpression," Cancer Research, 1999, vol. 59, pp. 2302-2306.

Feil R., et al., "Methylation Analysis on Individual Chromosomes: Improved Protocol for Bisulphite Genomic Sequencing," Nucleic Acids Research, 1994, vol. 22 (4), pp. 695-696.

Gonzalgo M.L., et al., "Rapid Quantitation of Methylation Differences at Specific Sites Using Methylation-Sensitive Single Nucleotide Primer Extension (Ms-SNuPE)," Nucleic Acids Research, 1997, vol. 25 (12), pp. 2529-2531.

Grigg G., et al., "Sequencing 5-methylcytosine Residues in Genomic DNA," BioEssays, 1994, vol. 16 (6), pp. 431-436.

Guatelli J.C., et al., "Isothermal, in Vitro Amplification of Nucleic Acids by a Multienzyme Reaction Modeled after Retroviral Replication," Proceedings of the National Academy of Sciences, 1990, vol. 87 (5), pp. 1874-1878.

Haines T.R., et al., "Allele-Specific Non-Cpg Methylation of the Nf1 Gene duirng Early Mouse Development," Developmental Biology, 2001, vol. 240 (2), pp. 585-598.

Hennig G., et al., "Mechanisms Identified in the Transcriptional Control of Epithelial Gene Expression," The Journal of Biological Chemistry, 1996, vol. 271 (1), pp. 595-602.

Herman J.G., et al., "Methylation-Specific PCR: A Novel PCR Assay for Methylation Status of Cpg Islands," Proceedings of the National Academy of Sciences, 1996, vol. 93 (18), pp. 9821-9826.

Hu X.C., et al., "E-Cadherin Promoter Methylation Can Regulate its Expression in Invasive Ductal Breast Cancer Tissue in Chinese Woman," Life Science, 2002, vol. 71 (12), pp. 1397-1404.

International Search Report and Written Opinion for Application No. PCT/US2014/025854, mailed on Jul. 7, 2014, 18 pages.

Jaenisch R., et al., "Epigenetic Regulation of Gene Expression: How the Genome Integrates Intrinsic and Environmental Signals," Nature Genetics, 2003, vol. 33, pp. 245-254.

Kumagai Y., et al., "Histone Deacetylase Inhibitor, Suberoylanilide Hydroxamic Acid (Vorinostat, SAHA) Profoundly Inhibits the Growth of Human Pancreatic Cancer Cells," International Journal of Cancer, 2007, vol. 121 (3), pp. 656-665.

Kwoh D.Y., et al., "Transcription-Based Amplification System and Detection of Amplified Human Immunodeficiency Viru: Type 1 with a Bead-Based Sandwixh Hybridization Format," Proceeding of the National Academy of Sciences of the USA, 1989, vol. 86 (4), pp. 1173-1177.

Leamon J.H., et al., "A Massively Parallel Picotiterplate Based Platform for Discrete Picoliter-scale Polymerase Chain Reactions," Electrophoresis, 2003, vol. 24 (21), pp. 3769-3777.

Lind G.E., et al., "A CpG Island Hypermethylation Profile of Primary Colorectal Carcinomas and Colon Cancer Cell Lines," Molecular Cancer, 2004, vol. 3:28, 11 pages.

Lizardi P.M., et al., "Exponential Amplification of Recombinant-RNA Hybridization Probes," Bio/Technology, 1988, vol. 6, pp. 1197-1202.

Lizardi P.M., et al., "Mutation Detection and Single-molecule Counting using Isothermal Rolling-circle Amplification," Nature Genetics, 1998, vol. 19 (3), pp. 225-232.

Lombaerts M., et al., "E-Cadherin Transcriptional Downregulation by Promoter Methylation but Not Mutation is Related to Epithelial-to-Mesenchymal Transition in Breast Cancer Cell," British Journal of Cancer, 2006, vol. 94 (5), pp. 661-671.

Maclean D., et al., "Application of 'next-generation' Sequencing Technologies to Microbial Genetics," Nature Reviews Microbiology, 2009, vol. 7 (4), pp. 287-296.

Marchevsky A.M., et al., "Classification of Individual Lung Cancer Cell Lines Based on DNA Methylation Markers: Use of Linear Discriminant Analysis and Artificial Neural Networks," Journal of Molecular Diagnostics, 2004, vol. 6 (1), pp. 28-36.

Margulies M., et al., "Genome Sequencing in Microfabricated High-Density Picolitre Reactors," Nature, 2005, vol. 437 (7057), pp. 376-380.

Martin V., et al., "Genomic Sequencing Indicates a Correlation Between DNA Hypomethylation in the 5' Region of the Ps2 Gene and its Expression in Human Breast Cancer Cell Lines," Gene, 1995, vol. 157 (1-2), pp. 261-264.

Miller C.A., et al., "Covalent Modification of DNA Regulates Memory Formation," Neuron, 2007, vol. 53 (6), pp. 857-869.

Mitra R.D., et al., "Fluorescent in Situ Sequencing on polymerase Colonies," Analytical Biochemistry, 2003, vol. 320 (1), pp. 55-65.

Mitra R.D., et al., "In Situ Localized Amplification and Contact Replication of Many Individual DNA Molecules," Nucleic Acids Research, 1999, vol. 27 (24), pp. e34.

Morozova O., et al., "Applications of Next-generation Sequencing Technologies in Functional Genomics," Genomics, 2008, vol. 92 (5), pp. 255-264.

Mullis K.B., et al., "Specific Synthesis of Dna In Vitro Via a Polymerase-catalyzed Chain Reaction," Methods in Enzymology, 1987, vol. 155, pp. 335-350.

Murakawa G.J., et al., "Direct Detection of HIV-1 RNA from AIDS and ARC Patient Samples," DNA: A Journal of Molecular Biology, 1988, vol. 7 (4), pp. 287-295.

Nakata S., et al., "The Methylation Status and Protein Expression of CDH1, P16 (INK4A), and Fragile Histidine Triad in Nonsmall Cell Lung Carcinoma: Epigenetic Silencing, Clinical Features, and Prognostic Significance," Cancer, 2006, vol. 106 (10), pp. 2190-2199.

Nelson N.C., et al., "Detection of Acridinium Esters by Chemiluminescence," in: Nonisotopic Probing, Blotting and Sequencing, 1995, Chapter 17, Academic Press, Inc., pp. 391-428.

Olek A., et al., "The Pre-Implantation Ontogeny of the H19 Methylation Imprint," Nature Genetics, 1997, vol. 17, pp. 275-276.

Pennisi E., "Genomics. Semiconductors Inspire New Sequencing Technologies," Science, 2010, vol. 327 (5970), pp. 1190.

Perler F.B., et al., "Thermostable Dna Polymerases," Advances in Protein Chemistry, 1996, vol. 48, pp. 377-435.

(56) References Cited

OTHER PUBLICATIONS

Persing, "In Vitro Nucleic Acid Amplification Techniques," Diagnostic Molecular Microbiology, 1993, pp. 51-77.
Rein T., et al., "Identifying 5-Methylcytosine and Related Modifications in DNA Genomes," Nucleic Acids Research, 1998, vol. 26 (10), pp. 2255-2264.
Reinhold W.C., et al., "Detailed DNA Methylation Profiles of the E-Cadherin Promoter in the NCI-60 Cancer Cells," Molecular Cancer Therapeutics, 2007, vol. 6 (2), pp. 391-403.
Shendure J., et al., "Accurate Multiplex Polony Sequencing of an Evolved Bacterial Genome," Science, 2005, vol. 309 (5741), pp. 1728-1732.
Thum O., et al., "Functionalized DNA: A New Replicable Biopolymer We Thank Dr. andreas Marx, University of Bonn, for Helpful Advice and Discussions. This Work was Supported by the Fonds Der Chemischen Industrie, the Karl-Ziegler Stiftung, and the Deutsche Forschungsgemeinschaft," Angewandte Chemie, 2001, vol. 40 (21), pp. 3990-3993.
Tucker K.L., "Methylated Cytosine and the Brain: A New Base for Neuroscience," Neuron, 2001, vol. 30 (3), pp. 649-652.
Voelkerding K.V., et al., "Next-Generation Sequencing: from Basic Research to Diagnostics," Clinical Chemistry, 2009, vol. 55 (4), pp. 641-658.
Walker G.T., et al., "Isothermal in Vitro Amplification of DNA by a Restriction Enzyme/DNA Polymerase System," Proceedings of the National Academy of Sciences, 1992, vol. 89 (1) pp. 392-396.
Weiss R., "Hot Prospect for New Gene Amplifier," Science, 1991, vol. 254 (5036), pp. 1292-1293.
Xiong Z., et al., "Cobra: A Sensitive and Quantitative DNA Methylation Assay," Nucleic Acids Research, 1997, vol. 25 (12), pp. 2532-2534.
Yoshiura K., et al., "Silencing of the E-Cadherin Invasion-Suppressor Gene by Cpg Methylation in Human Carcinomas," Proceedings of the National Academy of Sciences, 1995, vol. 92 (16), pp. 7416-7419.
Zeschnigk M., et al., "Imprinted Segments in the Human Genome: Different DNA Methylation Patterns in the Prader-Willi/Angelman Syndrome Region as Determined by the Genomic Sequencing Method," Human Molecular Genetics, 1997, vol. 6 (3), pp. 387-395.
Azzi S., et al., "Allele-specific Methylated Multiplex Real-time Quantitative PCR (ASMM RTQ-PCR), a Powerful Method for Diagnosing Loss of Imprinting of the 11p15 Region in Russell Silver and Beckwith Wiedemann Syndromes," Human Mutation, Feb. 2011, vol. 32 (2), pp. 249-258.
Fackler M.J., et al., "Quantitative Multiplex Methylation-specific PCR Assay for the Detection of Promoter Hypermethylation in Multiple Genes in Breast Cancer," Cancer Research, Jul. 1, 2004, vol. 64 (13), pp. 4442-4452.
He Q., et al., "Development of a Multiplex Methylight Assay for the Detection of Multigene Methylation in Human Colorectal Cancer," Cancer Genetics and Cytogenetics, Oct. 1, 2010, vol. 202 (1), pp. 1-10.
Supplementary European Search Report for Application No. EP14773416, mailed on Oct. 6, 2016, 10 pages.
First Office Action for Chinese Application No. 201480027133.6 mailed on Mar. 27, 2017, 16 pages.

* cited by examiner

MULTIPLEX METHYLATION-SPECIFIC AMPLIFICATION SYSTEMS AND METHODS

This application claims priority to Provisional Patent Application Ser. No. 61/782,370, filed Mar. 14, 2013, which is herein incorporated by reference in its entirety.

FIELD OF INVENTION

The present invention relates to systems and methods for performing multiplex amplification reactions. In particular, the present invention relates to multiplex methylation-specific amplification systems and methods.

BACKGROUND

DNA methylation is a type of chemical modification of DNA that can be inherited and subsequently removed without changing the DNA sequence. As such, it is part of the epigenetic code (Jaenisch & Bird. (2003) Nature Genetics, 33, 245, herein incorporated by reference in its entirety). DNA methylation involves the addition of a methyl group to a DNA nucleobase. In the most common example, a methyl group is added to the number 5 carbon of the cytosine pyrimidine ring. Cytosine methylation generally has the effect of reducing gene expression.

Methylation is a common capability of all viruses for self/non-self identification. DNA methylation at the 5 position of cytosine has been found in every vertebrate examined. In adult somatic tissues, DNA methylation typically occurs in a CpG dinucleotide context; non-CpG methylation is prevalent in embryonic stem cells (Dodge et al. (2002) Gene 289 (1-2): 41-48., Haines et al. (2001) Developmental Biology 240 (2): 585-598., herein incorporated by reference in their entireties). In plants, cytosines are methylated both symmetrically (CpG or CpNpG) and asymmetrically (CpNpNp). Long term memory storage in humans may be regulated by DNA methylation (Miller & Sweatt. (2007-Mar.-15) Neuron 53 (6): 857-869., Powell & Devin. (2008) New Scientist., herein incorporated by reference in their entireties).

In mammals, DNA methylation is essential for normal development and is associated with a number of key processes including imprinting, X-chromosome inactivation, suppression of repetitive elements and carcinogenesis. Between 60-90% of all CpGs are methylated in mammals (Tucker. (2001) Neuron. 30(3): 649-52., herein incorporated by reference in its entirety). CpGs are grouped in clusters called "CpG islands" that are present in the 5' regulatory regions of many genes. In many disease processes such as cancer, gene promoter CpG islands acquire abnormal hypermethylation, which results in heritable transcriptional silencing.

Methods for improving sensitivity and robustness of methylation detection assays are needed.

SUMMARY

The present invention relates to systems and methods for performing multiplex amplification reactions. In particular, the present invention relates to multiplex methylation-specific amplification systems and methods.

For example, in some embodiments, the present invention provides a method, comprising: a) treating a target nucleic acid with a methylation-specific detection reagent; b) simultaneously amplifying a plurality (e.g., 2, 3, 4, 5, 6, 7, 8, 9, 10, 11, 12, 13, 14, 15, 20, 25, 30, 2-30, 2-20, 3-20, 3-15, 4-20, 5-20, 6-20, 8-20, 10-20, etc.) of nucleic acid segments within the target nucleic acid to generate a plurality of amplicons; and c) detecting the plurality of amplicons. In some embodiments, the target comprises CpG islands. In some embodiments, the target is a promoter region of a gene. In some embodiments, the methylation specific reagent is bisulfite. In some embodiments, the simultaneous amplifying is carried out in a single reaction vessel (e.g., well, tube, etc.). In some embodiments, the nucleic acid target is GC-rich. In some embodiments, the bisulfite reacts with unmethylated cytosine residues, converting them to uracil residues and does not react with methylated cytosine residues, leaving them as 5-methylcytosine. In some embodiments, the amplification is PCR. In some embodiments, the detecting comprises contacting the amplicons with a plurality of nucleic acid probes. In some embodiments, the nucleic acid probes comprise a detectable label. In some embodiments, all of the probes comprise the same label. In some embodiments, the label is a fluorescent label, although other labels are contemplated. In some embodiments, the amplification and detection comprises real time PCR amplification and detection. In some embodiments, the detecting comprises a nucleic acid detection technique selected from, for example, mass spectroscopy, sequencing, or hybridization.

Further embodiments of the present invention provides a method, comprising: a) treating a target nucleic acid with a methylation-specific detection reagent; b) simultaneously amplifying at least 5 nucleic acid segments within the target nucleic acid to generate a plurality of amplicons; and c) detecting the plurality of amplicons.

Additional embodiments of the present invention provides a method, comprising: a) treating a target nucleic acid with a methylation-specific detection reagent; b) simultaneously amplifying at least 10 nucleic acid segments within the target nucleic acid to generate a plurality of amplicons; and c) detecting the plurality of amplicons.

In some embodiments, the present invention provides a method of amplifying nucleic acids, comprising: a) simultaneously amplifying a plurality of nucleic acid segments within a target nucleic acid that has been treated with a methylation-specific detection reagent to generate a plurality of amplicons; and b) detecting the amplicons.

In further embodiments, the present invention provides a method, comprising: a) treating a promoter nucleic acid with a methylation-specific detection reagent; b) simultaneously amplifying a plurality (e.g., 2, 3, 4, 5, 6, 7, 8, 9, 10, 11, 12, 13, 14, 15, 20, 25, 30, 2-30, 2-20, 3-20, 3-15, 4-20, 5-20, 6-20, 8-20, 10-20, etc.) of nucleic acid segments within the target nucleic acid to generate a plurality of amplicons; and c) detecting the plurality of amplicons.

In yet other embodiments, the present invention provides a method, comprising: a) treating a target nucleic acid with a bisulfite reagent; b) simultaneously amplifying a plurality (e.g., 2, 3, 4, 5, 6, 7, 8, 9, 10, 11, 12, 13, 14, 15, 20, 25, 30, 2-30, 2-20, 3-20, 3-15, 4-20, 5-20, 6-20, 8-20, 10-20, etc.) of nucleic acid segments within the target nucleic acid to generate a plurality of amplicons; and c) detecting the plurality of amplicons.

In still further embodiments, the present invention provides a method, comprising: a) treating a target nucleic acid with a methylation-specific detection reagent; b) simultaneously PCR amplifying a plurality (e.g., 2, 3, 4, 5, 6, 7, 8, 9, 10, 11, 12, 13, 14, 15, 20, 25, 30, 2-30, 2-20, 3-20, 3-15, 4-20, 5-20, 6-20, 8-20, 10-20, etc.) of nucleic acid segments within the target nucleic acid to generate a plurality of amplicons; and c) detecting the plurality of amplicons.

In some embodiments, the present invention provides a method, comprising: a) treating a target nucleic acid with a methylation-specific detection reagent; b) simultaneously amplifying a plurality (e.g., 2, 3, 4, 5, 6, 7, 8, 9, 10, 11, 12, 13, 14, 15, 20, 25, 30, 2-30, 2-20, 3-20, 3-15, 4-20, 5-20, 6-20, 8-20, 10-20, etc.) of nucleic acid segments within the target nucleic acid to generate a plurality of amplicons; and c) detecting the plurality of amplicons using a plurality of nucleic acid probes comprising the same label.

In some embodiments, the present invention provides systems, compositions, or kits, comprising reagents necessary, sufficient, or useful in the performing methylation-specific multiplex amplification reactions (e.g., primers, probes, bisulfite, buffers, and the like).

Additional embodiments will be apparent to persons skilled in the relevant art based on the teachings contained herein.

BRIEF DESCRIPTION OF THE DRAWING

FIG. 1 illustrates methylation-specific multiplex PCR of embodiments of the present disclosure. The solid black line (top) represents the sequence of a DNA target. The middle segmented black lines represent the sequence following bisufite treatment, which results in conversion of nonmethylated C's to U's and also fragmentation. Each of the short lines represents a unique amplicon with respect to the sequence of the target. The bottom lines represent amplicons that are targeted to different regions of the target nucleic acid.

DESCRIPTION OF THE FIGURES

FIG. 1 shows a schematic of amplification of a plurality of amplicons corresponding to a target nucleic acid.

DETAILED DESCRIPTION

The present invention relates to systems and methods for performing multiplex amplification reactions. In particular, the present invention relates to multiplex methylation-specific amplification systems and methods.

Definitions

To facilitate an understanding of the present technology, a number of terms and phrases are defined below. Additional definitions are set forth throughout the detailed description. As used herein, "a" or "an" or "the" can mean one or more than one. For example, "a" widget can mean one widget or a plurality of widgets.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the terms "subject" and "patient" refer to any animal, such as a dog, a cat, a bird, livestock, and particularly a mammal, and preferably a human.

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "amplicon" refers to a nucleic acid generated via amplification reaction. The amplicon is typically double stranded DNA; however, it may be RNA and/or DNA:RNA. The amplicon comprises DNA complementary to a sample nucleic acid. In some embodiments, primer pairs are configured to generate amplicons from a sample nucleic acid. As such, the base composition of any given amplicon may include the primer pair, the complement of the primer pair, and the region of a sample nucleic acid that was amplified to generate the amplicon. One skilled in the art understands that the incorporation of the designed primer pair sequences into an amplicon may replace the native sequences at the primer binding site, and complement thereof. In certain embodiments, after amplification of the target region using the primers the resultant amplicons having the primer sequences are used for subsequent analysis (e.g. base composition determination). In some embodiments, the amplicon further comprises a length that is compatible subsequent analysis.

The term "amplifying" or "amplification" in the context of nucleic acids refers to the production of multiple copies of a polynucleotide, or a portion of the polynucleotide, typically starting from a small amount of the polynucleotide (e.g., as few as a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood products, such as plasma, serum, and the like. Environmental samples include environmental material such as surface matter, soil, mud, sludge, biofilms, water, and industrial samples. Such examples are not however to be construed as limiting the sample types applicable to the present invention.

Embodiments of the Technology

Although the disclosure herein refers to certain illustrated embodiments, it is to be understood that these embodiments are presented by way of example and not by way of limitation.

Embodiments of the present disclosure provide systems and methods for multiplex methylation-specific PCR. In some embodiments, the systems and methods utilize more than one amplicon (e.g., 2 or more, 3, or more, 4 or more, 5 or more, 6 or more, 7 or more, 8 or more, 9 or more, 10 or more, 15 or more, 20 or more, etc.) for a specific methylated target (e.g., promoter or other nucleic acid, for example a CpG island). In some embodiments, between 2 and 30, 2 and 20, 2 and 15, 2 and 10, 5 and 30, 5 and 20, 5 and 10, or 5 and 10 amplicons are generated in a single reaction. In some embodiments, amplicons overlap or do not overlap.

Embodiments of the present disclosure are illustrated in FIG. 1. The present disclosure is illustrated with bisulfite PCR, although other methylation-specific detection or identification reagents or methods can be utilized. The solid black line (top) represents the sequence of a DNA target. The middle segmented black lines represent the sequence following bisufite treatment, which results in conversion of nonmethylated C's to U's and also fragmentation. Each of the short lines represents a unique amplicon with respect to the sequence of the target. The bottom lines represent amplicons that are targeted to different regions of the target nucleic acid.

In some embodiments, each amplicon is detected with a detectable label (e.g., fluorescently labeled probe or primer). In some embodiments, the labels for detecting each unique amplicon are the same. For example, in some embodiments, a probe with a fluorescent or other label is used for the analysis of the PCR process (e.g., real time PCR). In FIG. 1, 10 unique amplicons are shown, although the present disclosure is not limited to detection of 10 amplicons.

In some embodiments, all reactions are performed in a single tube or reaction vessel or volume (e.g., well, channel, etc.). In some embodiments, the amplicons selected for a given promoter are contiguous, overlap or a combination of overlapping and contiguous. In some embodiments, the assay is automated (e.g., using robotics).

The present disclosure is not limited to particular methylation detection or amplification methods. Exemplary methylation-specific detection methods, amplification methods, and detection methods are described below. Additional methods can be utilized in the systems and methods described herein.

I. Methylation Detection Technology

In some embodiments, the present disclosure provides systems and methods for detecting methylated DNA (e.g., multiplexed detection). Exemplary methylation-specific detection and amplification methods are described below.

A. Methylation-Specific Detection

In some embodiments, methylation analysis utilizes bisulfite conversion or Methylation Sensitive Restriction Enzyme (MSRE). Bisulfite conversion methods utilize sequencing, primer-probes, primer-gel, or primer-array analysis.

One method for analyzing DNA for 5-methyl cytosine is based on the specific reaction of bisulfite with cytosine which, upon subsequent alkaline hydrolysis, is converted to uracil which corresponds to thymidine in its base pairing behavior. 5-methylcytosine remains unmodified under these conditions. Consequently, the original DNA is converted in such a manner that methylcytosine, which originally cannot be distinguished from cytosine in its hybridization behavior, can now be detected, for example, by amplification and hybridization or sequencing. These techniques are based on base pairing which is now taken full advantage of.

An overview of methods of detecting 5-methylcytosines can be gathered from the following survey article: Rein, T., DePamphilis, M. L., Zorbas, H., Nucleic Acids Res. 1998, 26, 2255.

The bisulfite technology involves short specific fragments of a known gene, which are amplified subsequent to a bisulfite treatment and either completely sequenced (Olek, A. and Walter, J., Nat Genet. 1997, 17, 275-276) or individual cytosine positions are detected by a primer extension reaction (Gonzalgo, M. L., and Jones, P. A., Nucl. Acids Res. 1997, 25, 2529-2531, WO 9500669) or by an enzymatic digestion (Xiong, Z. and Laird, P. W., Nucl. Acids. Res. 1997, 25, 2532-2534). In addition, detection by hybridization has also been described (Olek et al., WO 99 28498).

Further publications dealing with the use of the bisulfite technique for methylation detection in individual genes are: Xiong, Z. and Laird, P. W. (1997), Nucl. Acids Res. 25, 2532; Gonzalgo, M. L. and Jones, P. A. (1997), Nucl. Acids Res. 25, 2529; Grigg, S. and Clark, S. (1994), Bioassays 16, 431; Zeschnik, M. et al. (1997), Human Molecular Genetics 6, 387; Teil, R. et al. (1994), Nucl. Acids Res. 22, 695; Martin, V. et al. (1995), Gene 157, 261; WO 97 46705; WO 95 15373 and WO 45560, herein incorporated by reference in their entireties. Using the bisulfate technique for detecting cytosine methylation in DNA samples is described in U.S. Pat. No. 7,524,629, herein incorporated by reference in its entirety.

Additional methods for determining methylation status are described, for example, in Lombaerts, M. et al. (2006) British Journal of Cancer. 94:661-671; Yoshiura, K. et al. (1995) Proc. Natl. Acad. Sci. 92:7416-7419; Lind, G. E. et al. (2004) Molecular Cancer 3:28; Kumagai, T. et al. (2007) Int. J. Cancer. 121:656-665; Hennig, G. et al. (1996) J. Biol. Chem. 271(1):595-602; Marchevsky, A. M. et al. (2004). Journal of Molecular Diagnostics 6:28-36; Reinhold, W. C. et al. (2007). Mol. Cancer. Ther. 6:391-403; Hu, X-C. et al. (2002) Life Sciences 71:1397-1404; or Nakata, S. et al. (2006) Cancer 106(10):2190-2199; each of which is herein incorporated by reference in its entirety. Commercial kits are also available for determination of promoter methylation status in tumor cells (e.g. Promoter Methylation PCR kit, from Panomics, Redwood City, Calif.).

Various methylation assay procedures are known in the art and can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, DMR, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

The term "MSP" (Methylation-specific PCR) refers to the art-recognized methylation assay described by Herman et al. (1996) Proc. Natl. Acad. Sci. USA 93: 9821-9826, and by U.S. Pat. No. 5,786,146.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, DMR, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

B. Amplification

In some embodiments, following or concurrently with methylation specific detection, nucleic acids are amplified. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

In some embodiments, amplification is isothermal amplification method. In some embodiments, amplification methods are solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule are used. In some embodiments, methods that rely on bridge PCR, where both PCR primers are attached to a surface (see, e.g., WO 2000/018957, U.S. Pat. Nos. 7,972,820; 7,790,418 and Adessi et al., Nucleic Acids Research (2000): 28(20): E87; each of which are herein incorporated by reference) are used. In some cases the methods of the invention can create a "polymerase colony technology", or "polony", referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003).

Examples of nucleic acid polymerases suitable for use in embodiments of the present invention include, but are not limited to, DNA polymerase (Klenow fragment, T4 DNA polymerase), thermostable DNA polymerases (Perler F. B. et al., Adv. Protein Chem. 1996, 48:377-435) identified and cloned in a variety of thermostable bacteria (such as Taq, VENT, Pfu, Tfl DNA polymerases) as well as their genetically modified derivatives (TaqGold, VENTexo, Pfu exo). Preferably the nucleic acid polymerase used for colony primer extension is stable under temperature at which the primer and template hybridization results specific enough to avoid incomplete or spurious amplifications of the template.

The amplification solution contains preferably, as nucleotide precursors, deoxyribonucleotide triphosphates, for example dATP, dTTP, dCTP, dGTP, naturally or non-naturally occurring, for example modified with a fluorescent or radioactive group. A large variety of synthetically modified nucleic acids have been developed for chemical and biological methods in order to increase the detectability and/or the functional diversity of nucleic acids. These functionalized/modified molecules can be fully compatible with natural polymerizing enzymes, maintaining the base pairing and replication properties of the natural counterparts, as recently reviewed (Thum 0 et al., Angew. Chem. Int. Ed. 2001, 40 (21): 3990-3993). Other components of the amplification solution are added consequently to the choice of the nucleic acid polymerase, and they are essentially corresponding to compounds known in the art as being effective to support the activity of each polymerase. The concentration of compounds like dimethyl sulfoxide (DMSO), Bovine Serum Albumin (BSA), Triton X-100, or $MgCl_2$ is well known in the prior art as being important to have an optimal amplification, and therefore the operator can easily adjust such concentrations for the methods of the present invention on the basis of the examples presented hereafter.

In some embodiments, amplification reactions amplify multiple segments of a target. In some embodiments, the segments do not overlap. In some embodiments, segments overlap by one or more nucleotides. In some embodiments, amplicons are staggered. In some embodiments, amplicons are continuous.

In some embodiments, amplification reactions generate 2, 3, 4, 5, 6, 7, 8, 9, 10, 11, 12, 13, 14, 15, 20, 25, 30, 35, 40, 45, or 50 or more amplicons. In some embodiments, between 2 and 30, 2 and 20, 2 and 15, 2 and 10, 5 and 30, 5 and 20, 5 and 10, or 5 and 10 amplicons are generated in a single reaction.

In some embodiments, nucleic acid targets are genes, promoter regions of genes, or other nucleic acids. In some embodiments, targets comprise CpG islands.

C. Detection

In some embodiments, amplified nucleic acids are detected by binding of a labeled probe to the nucleic acids. In some embodiments, detection is real time detection (e.g., simultaneous with amplification). Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DAB-CYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety). In some embodiments, capillary electrophoresis (CE) is utilized to analyze nucleic acid fragment. During capillary electrophoresis, nucleic acids (e.g., the products of a PCR reaction) are injected electrokinetically into capillaries filled with polymer. High voltage is applied so that the fluorescent DNA fragments are separated by size and are detected by a laser/camera system. In some embodiments, CE systems from Life Technogies (Grand Island, N.Y.) are utilized for fragment sizing (See e.g., U.S. Pat. No. 6,706,162, U.S. Pat. No. 8,043,493, each of which is herein incorporated by reference in its entirety).

In some embodiments, probes and/or primers utilized in detection methods are labeled. In some embodiments, the probe/primer is biotinylated and the tag binding reagent is a streptavidin reagent, such as a streptavidin bead. Replicated nucleic acid strands comprising the biotinylated primer (e.g., the primer extension product resulting from extension of the biotinylated primer) are isolated by contacting the strands with the streptavidin beads. Any combination of tagged primer and tag binding reagent may be utilized. Other suitable examples include haptenylated primers and beads or other reagents comprising an antibody or other antigen binding protein that binds to the hapten. Suitable haptens include, but are not limited to, pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by Podophyllotoxin and Podophyllotoxin derivatives; and combinations thereof. Specific examples of haptens include, but are not limited to, 2,4-Dintrophenyl (DNP), Biotin, Fluorescein derivatives (FITC, TAMRA, Texas Red, etc.), Digoxygenin (DIG), 5-Nitro-3-pyrozole-carbamide (nitropyrazole, NP), 4,5,-Dimethoxy-2-nitrocinnamide (nitrocinnamide, NCA), 2-(3,4-Dimethoxyphenyl)-quinoline-4-carbamide (phenylquinolone, DPQ), 2,1,3-Benzoxadiazole-5-carbamide (benzofurazan, BF), 3-Hydroxy-2-quinoxalinecarbamide (hydroxyquinoxaline, HQ), 4-(Dimethylamino)azobenzene-4'-sulfonamide (DAB-SYL), Rotenone isoxazoline (Rot), (E)-2-(2-(2-oxo-2,3-dihydro-1H-benzo[b][1,4]diazepin-4-yl)phenozy)acetamide (benzodiazepine, BD), 7-(diethylamino)-2-oxo-2H- chromene-3-carboxylic acid (coumarin 343, CDO), 2-Acetamido-4-methyl-5-thiazolesulfonamide (thiazolesulfonamide, TS), and p-Mehtoxyphenylpyrazopodophyllamide (Podo).

In some embodiments, nucleic acids are detected and characterized by the identification of a unique base composition signature (BCS) using mass spectrometry (e.g., Abbott PLEX-ID system, Abbot Ibis Biosciences, Abbott Park, Ill.,) described in U.S. Pat. Nos. 7,108,974, 8,017,743, and 8,017,322; each of which is herein incorporated by reference in its entirety.

In some embodiments, nucleic acid sequencing methods are utilized for detection. In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S.

Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., Clinical Chem., 55: 641-658, 2009; MacLean et al., Nature Rev. Microbiol., 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781, 166; each incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, detection methods utilize hybridization assays. Illustrative non-limiting examples of nucleic acid hybridization techniques include, but are not limited to, microarrays including, but not limited to: DNA microarrays (e.g., cDNA microarrays and oligonucleotide microarrays). A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts by comparing gene expression in disease and normal cells. Microarrays can be fabricated using a variety of technologies, including but not limiting: printing with fine-pointed pins onto glass slides; photolithography using premade masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

D. Analysis

In some embodiments, a computer-based analysis program is used to translate the raw data generated by the detection assay (e.g., methylation levels of a nucleic acid) into data of predictive value for an end user (e.g., medical personnel). The user can access the predictive data using any suitable means. Thus, in some preferred embodiments, the present invention provides the further benefit that the user, who is not likely to be trained in genetics or molecular biology, need not understand the raw data. The data is presented directly to the end user in its most useful form. The user is then able to immediately utilize the information in order to determine useful information (e.g., in medical diagnostics, research, or screening).

The present invention contemplates any method capable of receiving, processing, and transmitting the information to and from laboratories conducting the assays, information provides, medical personal, and subjects. For example, in some embodiments of the present invention, a sample (e.g., blood, cell or tissue sample) is obtained from a subject and submitted to a profiling service (e.g., lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a cheek swab) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (e.g., methylation data), specific for the information desired for the subject. The data is then prepared in a format suitable for interpretation by the end user (e.g., medical personnel). For example, rather than providing raw data, the prepared format may represent a conclusion or assessment (e.g., risk of cancer developing or likelihood of cancer being present) for the subject. The data may be displayed to the user by any suitable method. For example, in some embodiments, the profiling service generates a report that can be printed for the user or displayed on a computer monitor.

In some embodiments, the information is first analyzed at a local medical facility or at a regional facility. The raw data is then sent to a central processing facility for further analysis and/or to convert the raw data to information useful for the user. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the end user, the subject, or researchers.

E. Systems and Kits

In some embodiments, the present invention provides kits and systems for the amplification and/or analysis of nucleic acids. In some embodiments, kits include reagents necessary, sufficient or useful for analysis and detection of methylated nucleic acids (e.g., primers, probes, solid supports, reagents, controls, instructions, etc.). For example, in some embodiments, kits comprise pairs of primer for amplification of multiple amplicons of a target. In some embodiments, kits comprise multiple labeled probes (e.g., comprising the same or different labels). In some embodiments, kits comprise reagents for methylation-specific detection (e.g., bisulfite reagents). In some embodiments, systems include automated sample and reagent handling devices (e.g., robotics).

II. Uses

The systems and methods described herein find use in a variety of research, screening, and diagnostic applications. In some embodiments, the multiplex methylation specific amplification methods described above are utilized for predicting a predisposition to a disease in a subject, diagnosing a disease in a subject, predicting the likelihood of recurrence of disease in a subject, providing a prognosis for a subject with a disease, or selecting a subject with a disease for treatment with a particular therapy. These processes preferably comprise providing a genomic DNA sample from a subject; and detecting the methylation status of predetermined regions of the genomic DNA sample by the processes described above. In some embodiments, an altered level of 5-hydroxymethylcytosine and/or 5-methylcytosine methylation (e.g., a higher or lower level) of the predetermined regions of the genomic DNA to a reference methylation status provides an indication selected from the group consisting of an indication of a predisposition of the subject to a disease, an indication that the subject has a disease, an indication of the likelihood of recurrence of a disease in the subject, an indication of survival of the subject, and an indication that the subject is a candidate for treatment with a particular therapy.

In some embodiments, the systems and methods described herein target methylated gene promoters. Gene promoters are frequently methylated in cancer patients and this methylation has been shown to be associated with an inhibition of transcription of the associated gene. Gene promoters can vary in size from approximately 500 bases to greater than 1000 bases. In some embodiments that utilize PCR assays the amplicon size is usually 100 base pairs or less. Thus, in some embodiments, several amplicons are targeted for a specific gene promoter or other target nucleic acid. In some embodiments, multiple amplicons are generated in a single PCR reaction well or tube. In some embodiments, the same type of signaling molecule (e.g., fluorophore) is used for each unique probe. This results in an increase in signal, relative to an amplification reaction that uses a single probe that was associated with a single amplicon, thus leading to an increase in assay sensitivity relative to methods that utilize a single amplicon. In some embodiments, both unique strands of non-complimentary DNA that are generated by bisulfite conversion of native double stranded DNA.

The systems and methods described herein find use in any number of methylation detection assays. In some embodiments, the multiplex methods are used in promoter methylation assays to detect disease (e.g., cancer).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A method, comprising:
   a) treating a specific target nucleic acid with a methylation-specific detection reagent, wherein the specific target nucleic acid is a single gene or untranslated region of a single gene;
   b) simultaneously amplifying a plurality of different nucleic acid segments within said specific target nucleic acid to generate a plurality of different amplicons wherein said simultaneous amplifying is carried out in a single reaction vessel; and
   c) detecting two or more amplicons of said plurality of different amplicons comprising said different nucleic acids segments within said specific target nucleic acid wherein said detecting comprises contacting said plurality of different amplicons comprising said different nucleic acids segments within said specific target nucleic acid with a plurality of different nucleic acid probes wherein said plurality of different nucleic acid probes comprise a detectable label that is the same label in each of said plurality of different nucleic acid probes.

2. The method of claim 1, wherein said target nucleic acid is a promoter region of a gene.

3. The method of claim 1, wherein said methylation specific reagent is bisulfite.

4. The method of claim 1, wherein said nucleic acid target is GC-rich.

5. The method of claim 4, wherein said nucleic acid target comprises CpG islands.

6. The method of claim 1, wherein said amplification is PCR.

7. The method of claim 1, wherein said amplification and detection comprises real time PCR amplification and detection.

8. The method of claim 1, wherein said detecting comprises detecting hybridization of at least two detectably labeled probes of said plurality of different nucleic acid probes to at least two amplicons of the plurality of different amplicons.

9. The method of claim 1, wherein said plurality of different amplicons comprises at least 5 amplicons.

10. The method of claim 1, wherein said plurality of different amplicons comprises at least 10 amplicons.

11. A method, comprising:
   a) treating a specific target nucleic acid with a methylation-specific detection reagent;
   b) simultaneously amplifying a plurality of different nucleic acid segments within said specific target nucleic acid to generate a plurality of different amplicons comprising said different nucleic acids segments within said specific target nucleic acid wherein said simultaneous amplifying is carried out in a single reaction vessel; and
   c) contacting said amplicons with a plurality of different nucleic acid probes to detect said plurality of amplicons comprising said different nucleic acids segments within said specific target nucleic acid wherein said plurality of different nucleic acid probes comprise a detectable label that is the same label in each of said plurality of different nucleic acid probes.

* * * * *